(12) United States Patent
Frei et al.

(10) Patent No.: US 6,530,928 B1
(45) Date of Patent: Mar. 11, 2003

(54) INSTRUMENT, INSTRUMENT SET AND A METHOD FOR THE INTRODUCTION OF AN OSTEOCHONDRAL TRANSPLANT

(75) Inventors: Heribert Frei, Winterthur; Daniel Roder, Evilard; Roland P. Jakob, Môtier, all of (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/533,874

(22) Filed: Mar. 22, 2000

(30) Foreign Application Priority Data

Mar. 23, 1999 (EP) .............................. 99810259

(51) Int. Cl.⁷ .............................................. A61B 17/58
(52) U.S. Cl. .............................. 606/99; 606/96; 606/80; 606/88
(58) Field of Search .............................. 606/99, 96, 53, 606/86, 185, 80, 88

(56) References Cited

U.S. PATENT DOCUMENTS

| | | | |
|---|---|---|---|
| 5,632,747 A | | 5/1997 | Scarborough et al. |
| 5,718,707 A | | 2/1998 | Mikhail |
| 5,868,711 A | * | 2/1999 | Kramer et al. ............ 606/185 |
| 5,919,196 A | * | 7/1999 | Bobic et al. ................ 606/96 |
| 6,013,082 A | * | 1/2000 | Hiernard et al. ............ 606/99 |
| 6,146,385 A | * | 11/2000 | Torrie et al. ............... 606/99 |

FOREIGN PATENT DOCUMENTS

| | | |
|---|---|---|
| DE | 2 311 521 | 9/1973 |
| DE | 195 03 504 A1 | 3/1996 |
| EP | 0 470 393 A1 | 2/1992 |
| EP | 0 824 893 A2 | 2/1998 |
| FR | 2 398 490 | 2/1979 |
| FR | 2 716 375 | 8/1994 |
| WO | WO 96/27333 | 9/1996 |
| WO | WO 98/34569 | 8/1998 |

* cited by examiner

*Primary Examiner*—Pedro Philogene
(74) *Attorney, Agent, or Firm*—Townsend and Townsend and Crew LLP

(57) ABSTRACT

An instrument (2, 3) for the introduction of an osteochondral transplant (P) which is removed form a harvest location, or of an implant which is correspondingly prepared in vitro at an implantation location, has a passage (201, 301) in which the transplant is received and a piston (31) for the pressing out of the transplant (P) from the distal end of the passage into a depression which is prepared at the implantation location. A space for the reception of a buffer medium (F) with a high conformability and an elasticity which is dimensioned in such a manner that no bodily contact between the piston (31) and the transplant (P) or the implant respectively exists during the pressing out of the transplant (P) is provided between the end surface (311) of the piston (31) facing the transplant (P) and the surface of the transplant (P) facing the piston (31).

12 Claims, 6 Drawing Sheets

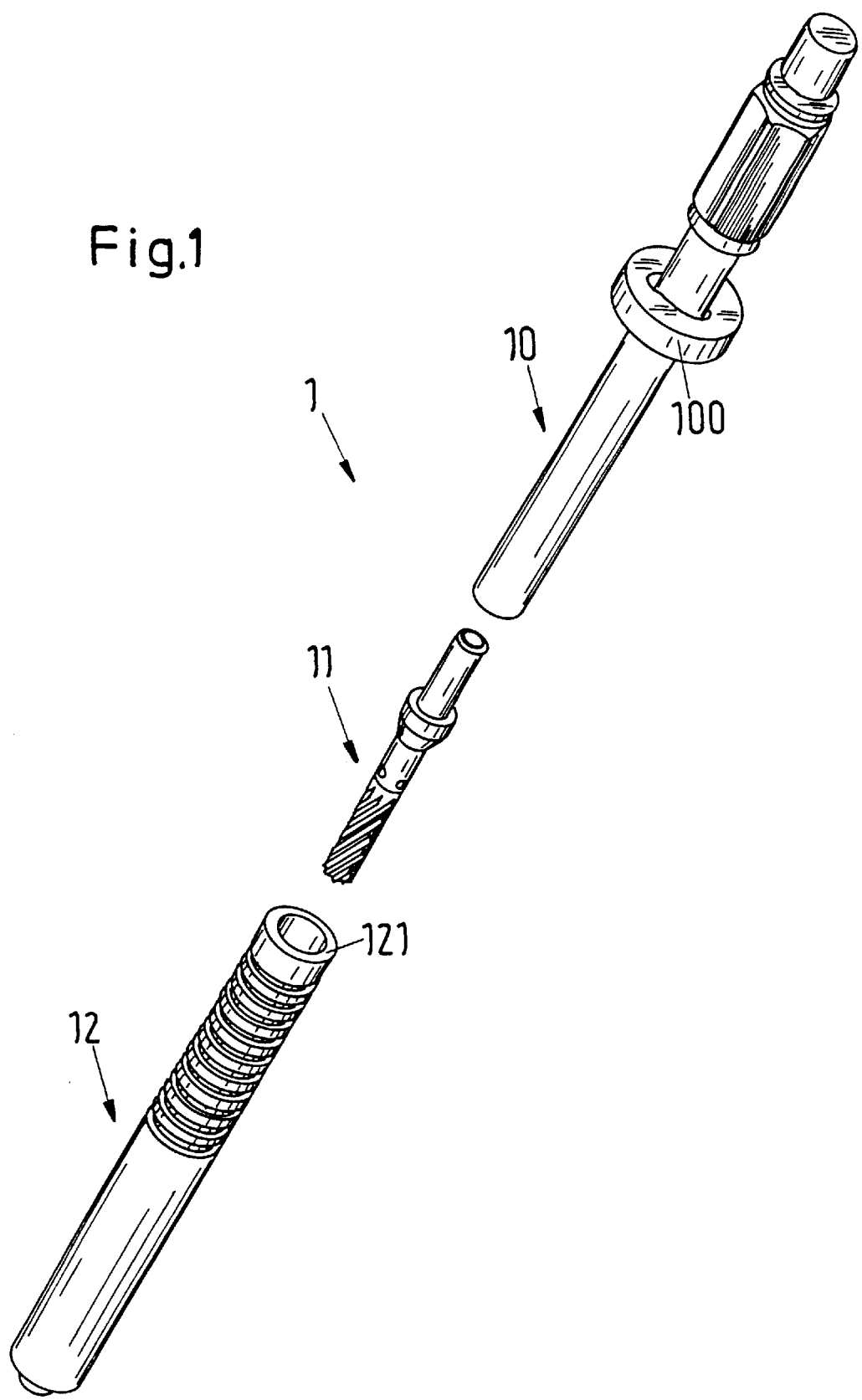

Figure 3:
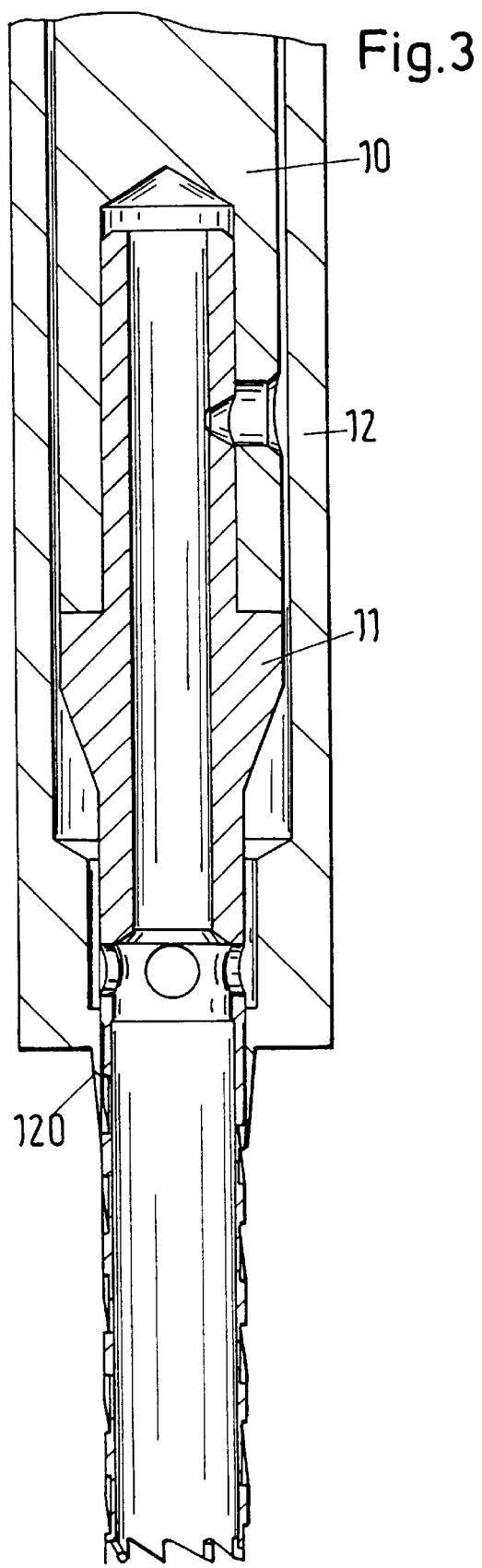

Fig. 5
Fig. 6
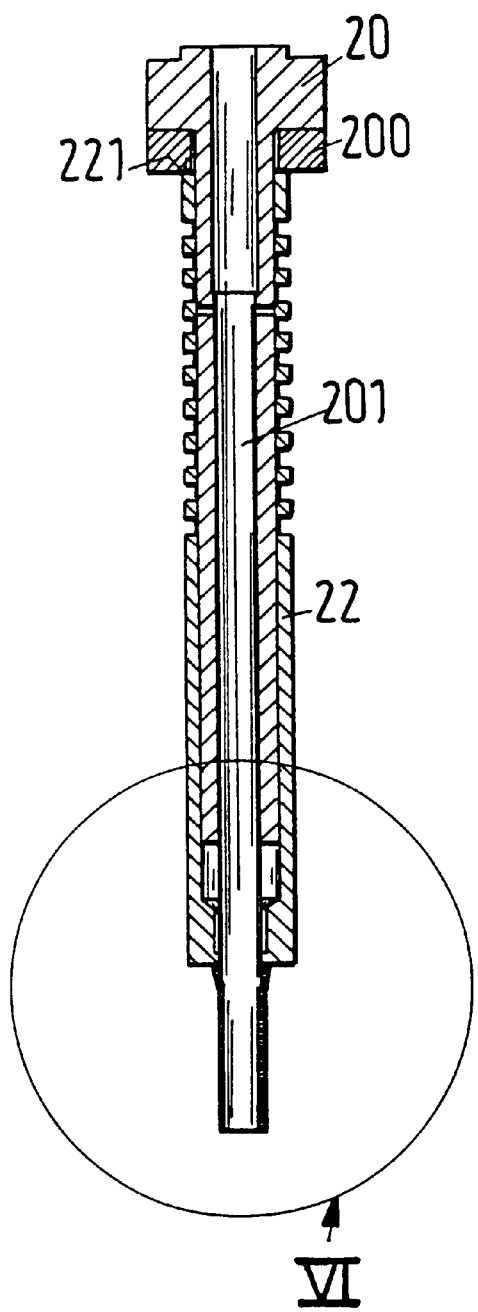
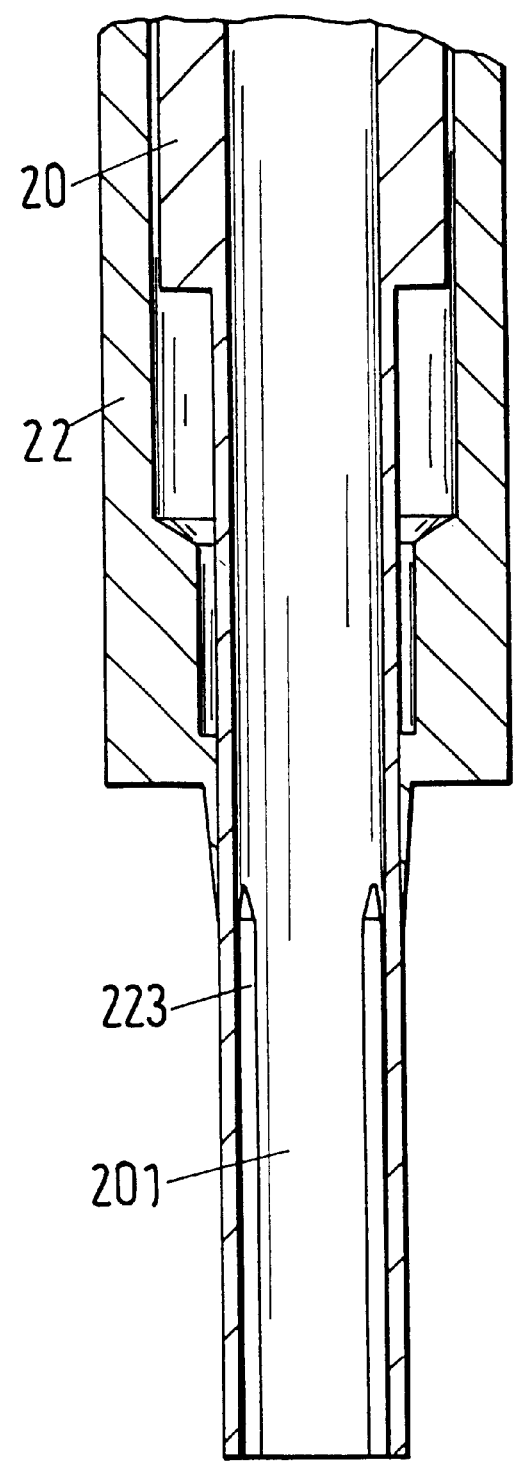

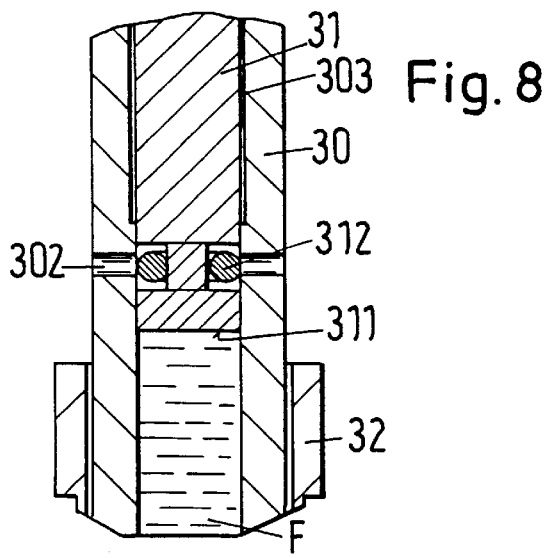
Fig. 8
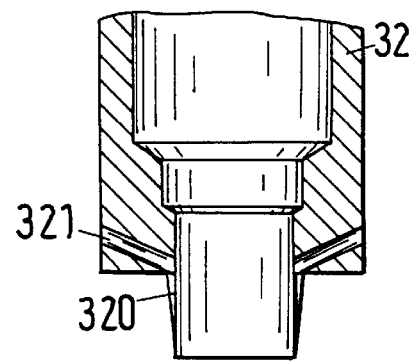
Fig. 9
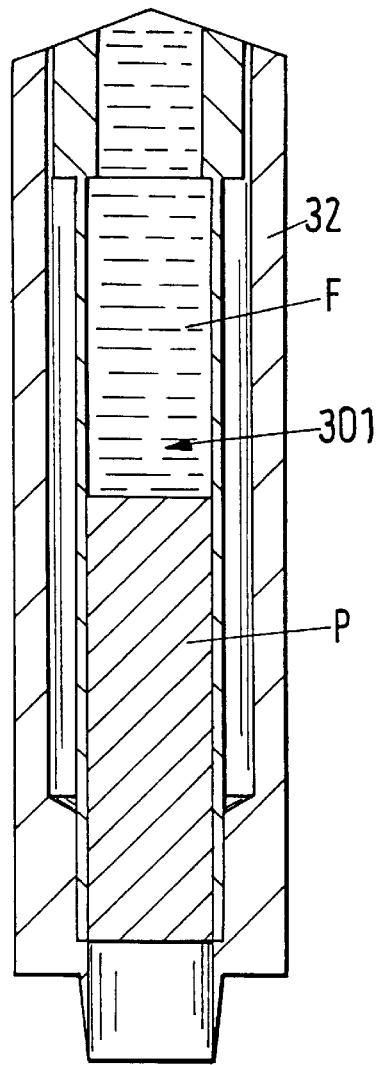

INSTRUMENT, INSTRUMENT SET AND A METHOD FOR THE INTRODUCTION OF AN OSTEOCHONDRAL TRANSPLANT

The invention relates to an instrument, to an instrument set and to a method for the introduction of an osteochondral transplant, or of an implant which is correspondingly prepared in vitro respectively, in accordance with the preamble of the respective independent claim.

The treatment of cartilage defects with the help of transplantation of osteochondral transplants is a kind of treatment which is increasingly being used in recent times with success. This treatment takes place essentially in that one or more depressions (e.g. blind bores) are first made at the defect location, e.g. by means of a suitable borer. Then transplants such as e.g. bone pegs which have an intact cartilage layer are removed at a harvest location (the harvest location is preferably more or less unstressed). These bone pegs are then introduced into the blind bore which had been made at the defect location. With time the peg grows together with intact cartilage and bone. Depending on the size of the defect a plurality of blind bores can also be made at the defect location and a plurality of pegs used accordingly because the lateral distances (gaps) between the cartilage layer of the transplants and the intact cartilage about the defect location must not become too large. Instead of the transplant a cartilage implant which is cultivated in vitro can also be implanted at the defect location. The surrounding intact cartilage grows together in this case with the cartilage which is cultivated in vitro.

The introduction of a peg—in the following the term "peg" will always be used both for a transplant and for an implant—takes place in the known manner that the peg which is located in a passage of the corresponding instrument is pressed out of the instrument into the blind bore with the help of a piston. For this the front surface of the piston is pressed against the surface of the peg facing the piston and the piston is pushed forwards—the piston is thus located in bodily contact with the cartilage surface of the peg and exerts a force on this cartilage surface in this procedure.

Cartilage cells—chondrocytes—are sensitive to excessive surface pressings, thus to excessive forces which act on surfaces which are too small. If a surface pressing which is typically permissible for the cartilage cells is exceeded, then the cartilage cells or the cartilage tissue respectively can be damaged. Damaged cartilage hardly regenerates. Moreover, cartilage is also sensitive in regard to deformation, which means that in a non-uniform stressing by forces a cartilage deformation takes place (through which the cartilage can likewise be damaged).

On the other hand cartilage surfaces of pegs are usually convex, seldom concave, almost never planar, often sometimes even slanted (inclined). As a result the cartilage surface and the usually planar front surface of the piston are incongruent and there often results a point or line shaped contact so that at the location of the contact a high surface pressing results. In addition the blind bore at the defect location has a slight under-dimensioning relative to the peg so that the peg sits in a press seating in the blind bore after the introduction. Since the piston is pressed forwards during the introduction of the peg into the blind bore through mild strikings against the proximal end of the piston, the static friction between the peg and the wall of the blind bore must be overcome each time (stop and go). This leads to a still higher stressing of the cartilage surface and can result in damage to the cartilage.

Through the friction between the piston and the cartilage surface, shear strains also arise in addition to the stresses as a result of the striking impulse which can damage the cartilage cells or the cartilage tissue respectively. This is likewise a result of the incongruence of the cartilage surface and the front surface of the piston. Since damaged cartilage hardly regenerates, the result of the transplantation—and thus the benefit to the patient—is in such cases slight. In some cases the introduction of pegs with slanted (inclined) surface even proves impossible.

Here the invention wishes to provide a remedy. The object of the present invention is therefore to propose an instrument and an instrument set respectively by means of which it is possible to drive in an osteochondral transplant or an implant which is correspondingly prepared in vitro independently of the shape of the cartilage surface in a depression which is made at the defect location (e.g. the blind bore mentioned) without damaging the cartilage surface of the transplant or the implant respectively in the process or deforming it (through which the cartilage can likewise be damaged).

This object is satisfied by the method and the instrument or the instrument set respectively such as is characterised by the features of the respective patent claim. Particularly advantageous embodiments result from the features of the subordinate patent claims.

In this it should be mentioned in advance that not only a corporeal piston is to be understood by a "piston" in the sense of the present invention, but rather in general a means for the exerting of forces or of pressure respectively on the buffer medium. This can e.g. also be done with the help of a pump without a corporeal piston coming into contact with the buffer medium.

In accordance with the invention a space for the reception of a buffer medium with a high conformability is provided between the end surface of the piston facing the transplant or implant respectively (in the following for the sake of simplicity reference will be made only to the transplant) and the surface of the transplant facing the piston so that the buffer medium can adapt in an ideal manner at the boundary to the surface of the transplant to the shape of this surface. Furthermore, the buffer medium has an elasticity which is dimensioned in such a manner that no bodily contact between the piston and the transplant exists during the pressing out of the transplant. Through the ideal adaptation of the buffer medium to the shape of the surface of the transplant it is achieved that the surface pressing is as small as possible (the forces are transmitted approximately homogeneously over the entire surface of the transplant). On the other hand a mechanical contact between the piston and the transplant is avoided through the elasticity of the buffer medium so that an incongruent contact of the piston onto the surface of the transplant can not arise. In this way transplants or implants respectively with any desired surface can be driven in into the depressions (e.g. blind bores) at the defect location without it being possible for the transplant surface to be damaged or deformed (and thereby possibly damaged) in the process.

In an advantageous exemplary embodiment the piston is provided with abutment means which define an end position of the piston and prevent a further pushing forward of the piston beyond the end position. Through this it can on the one hand be avoided that the transplant is further stressed by forces beyond a desired end position. If the transplant has namely e.g. been driven in into the depression at the defect location up to a desired depth (not necessarily up to the base of the depression), then it should not be possible to drive in the transplant further into the depression through the further exertion of forces or; respectively, it should not be possible to damage the surface of the transplant through the exertion of excessive surface pressings, such as can arise when the transplant has already been driven in up to the base of the depression, but the transplant is nevertheless stressed with increasingly large surface pressings through further pushing forward of the piston. Here the (preferably adjustable) abutment provides a remedy in that it prevents a further pushing forward of the piston.

In a further advantageous exemplary embodiment the buffer medium is a fluid, in particular a liquid, and the piston is provided with a sealing means which seals off the passage and prevents a backward flowing of fluid in the proximal direction during the pushing forward of the piston in the distal direction. Liquids are particularly preferred because on the one hand they are substantially incompressible and thus reliably prevent a bodily contact between the piston and the surface of the transplant, but however on the other hand adapt ideally to the shape of the surface of the transplant and thus provides for a minimum surface pressing. Body compatible liquids such as e.g. a Ringer solution (a flushing solution which is usually used in the operating room) or a sodium chloride solution (cooking salt) are preferably used as liquids. During the pushing forward of the piston the liquid is driven ahead of the piston and ideally transmits the force to the surface of the transplant independently of the shape of the transplant surface.

In a further development of this exemplary embodiment the sealing means is designed as an O-ring which is arranged in the distal end region of the piston, and indeed proximally to the end surface of the piston facing the transplant. Through this the entire front surface of the piston is available for the transmission of the forces to the liquid, which in turn provides for an ideal transmission of the forces onto the transplant surface.

In a further development of this exemplary embodiment the instrument comprises a sleeve which is provided at its distal end with a cutting edge. In the wall of the sleeve directly following the proximal end of the cutting edge, passage openings are provided which enable an emergence of the fluid as soon as the proximal end of the transplant frees the passage openings during the pressing out of the transplant. In this way it can be achieved that the transplant can no longer or can only to a minimal extent be driven further in after the passing of the passage openings since the liquid can escape through the passage openings and thus the forces are no longer transmitted to the transplant. The operating surgeon notices this through the sudden decrease of the resistance and then knows that the transplant has now been driven in up the desired depth. In this way a kind of non-mechanical "depth abutment" can thus be realised. In addition mechanical abutment means (see above) can also quite well be provided in order to reliably avoid a bodily contact between the piston and the transplant, should the piston happen to be pushed further forward in spite of the reaching of the non-mechanical "depth abutment".

In a further particularly advantageous exemplary embodiment of the instrument the piston can be coupled at its proximal end to a drive which produces a continuous forward thrust of the piston. If namely the transplant—as initially described—is in each case always driven only a bit of the way with the help of an impulse striking but then comes to rest before it is driven in a further bit of the way with the help of the next impulse striking, then the static friction must be overcome in each case. If in contrast the transplant is continuously driven in, then the static friction need be overcome only once (namely at the beginning) and then only the sliding friction need be overcome, which is lower than the static friction, through which the stress on the transplant surface is further reduced.

Alternatively to the already named fluids, in particular to the liquids, the buffer medium can also be designed as a soft plastic or as a sponge-like plastic, the elastic module of which is smaller than the elastic module of the softest part of the transplant or implant, with it being possible where appropriate for the plastic to be filled with a liquid. As a result of the lower elastic module the buffer medium can first ideally adapt to the shape of the surface of the transplant and then transmits (after a certain compression of the buffer medium has been reached) the forces ideally to the transplant surface. E.g. a balloon which is filled with fluid, in particular liquid, also comes under consideration as a buffer medium.

The instrument set in accordance with the invention comprises an instrument for the removal of a transplant at a harvest location or, respectively, for the removal of the implant which is produced in vitro from a corresponding container. Furthermore, the instrument set comprises an instrument for the production of a depression at the implantation location and an instrument for the introduction of the removed transplant at the implantation location. The instrument for the introduction of the transplant is designed in this in accordance with one of the above explained exemplary embodiments.

In a preferred further development of the instrument set the instrument for the removal of the transplant or the implant respectively is also designed in accordance with one of the above explained exemplary embodiments. In particular it can be the case that the instrument or at least parts thereof can be used both for the removal (extraction) of the transplant and for the introduction (implantation) of the transplant.

Finally the invention also relates to a method for the transplantation of an osteochondral transplant or, respectively, for the implantation of a corresponding implant which is prepared in vitro, in which a depression is first produced at the implantation location for the reception of the transplant or the implant respectively, then the transplant is removed at a harvest location or the implant is removed from a corresponding container respectively, and finally the transplant or the implant respectively is introduced into the depression produced at the implantation location. In this method an instrument in accordance with any one of the above explained exemplary embodiments is used. In an advantageous embodiment of this method, during the introduction of the transplant or the implant respectively, which is located in the passage of the instrument, into the depression from the proximal side, first the buffer medium and then the piston are introduced into the passage so that the enclosed buffer medium drives the transplant or the implant respectively out of the instrument into the depression when the piston is pushed forward in the distal direction. The operating surgeon can thus first bring the instrument together with the transplant which is located in the passage of the instrument into the desired position, then introduce the buffer medium (e.g. the Ringer solution mentioned) and finally place the piston on and push it forward so that with the help of the pressure which is exerted on the buffer medium the transplant is driven in into the depression.

Figure 2:
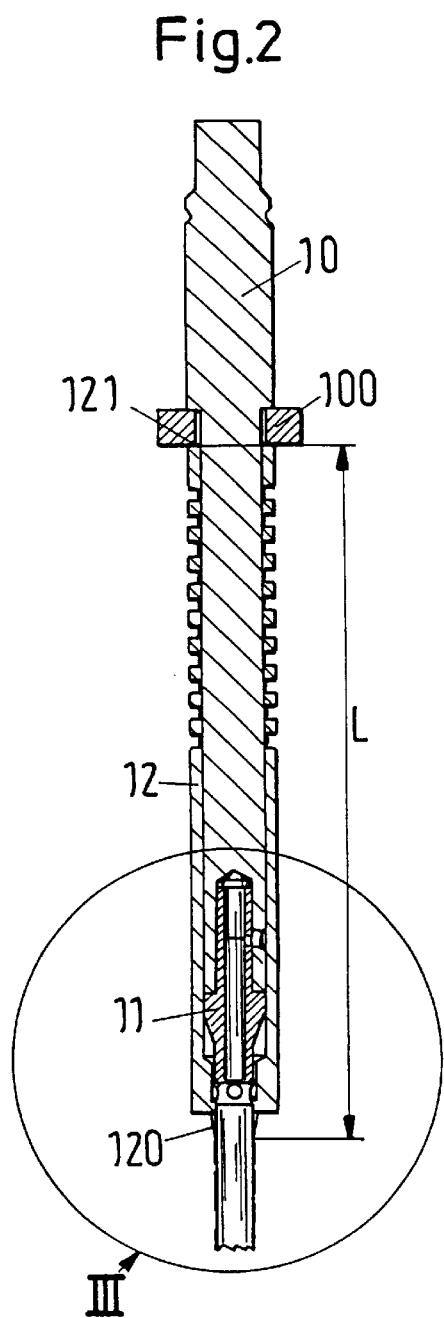
Figure 4:
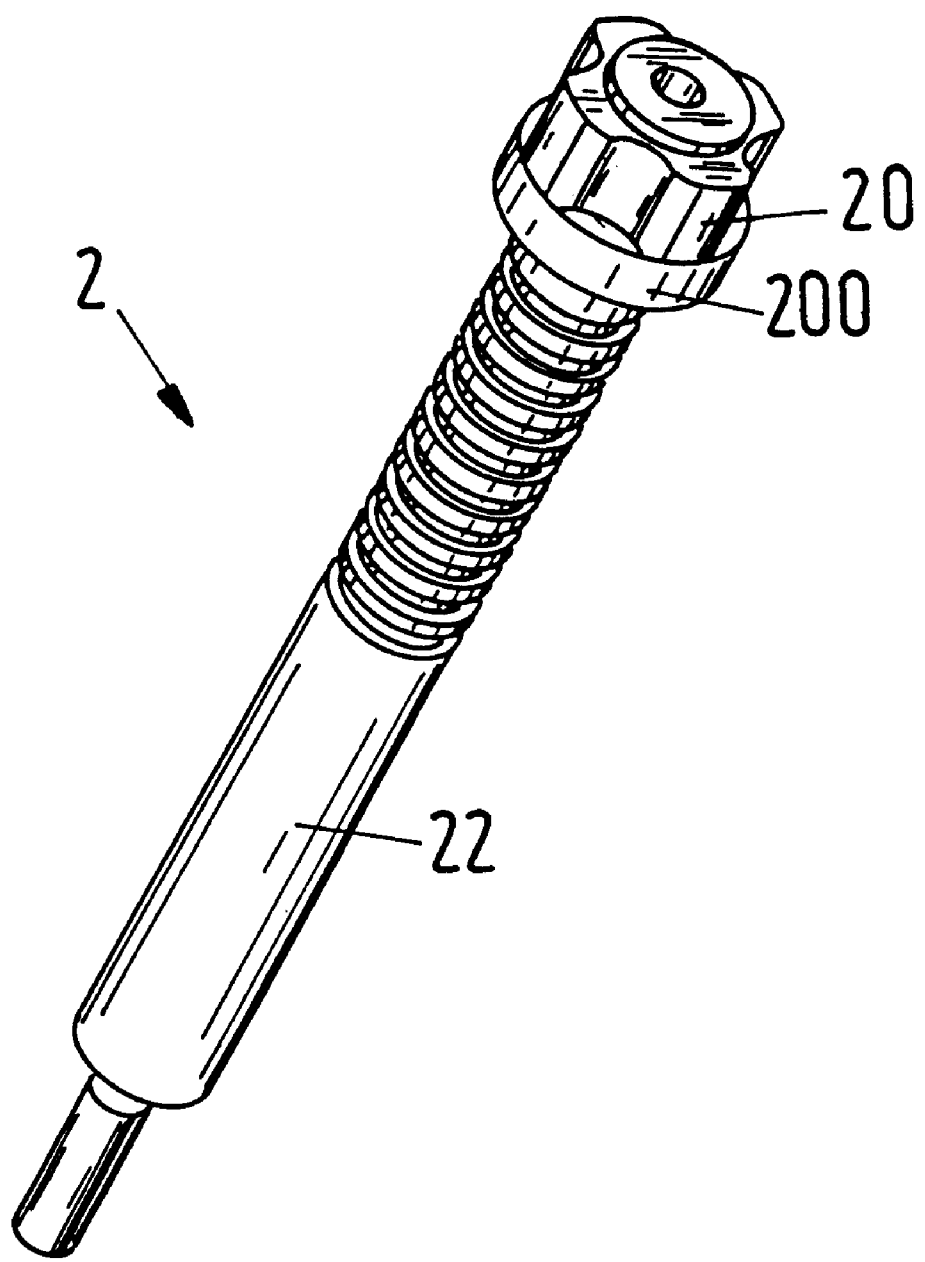
Figure 7:
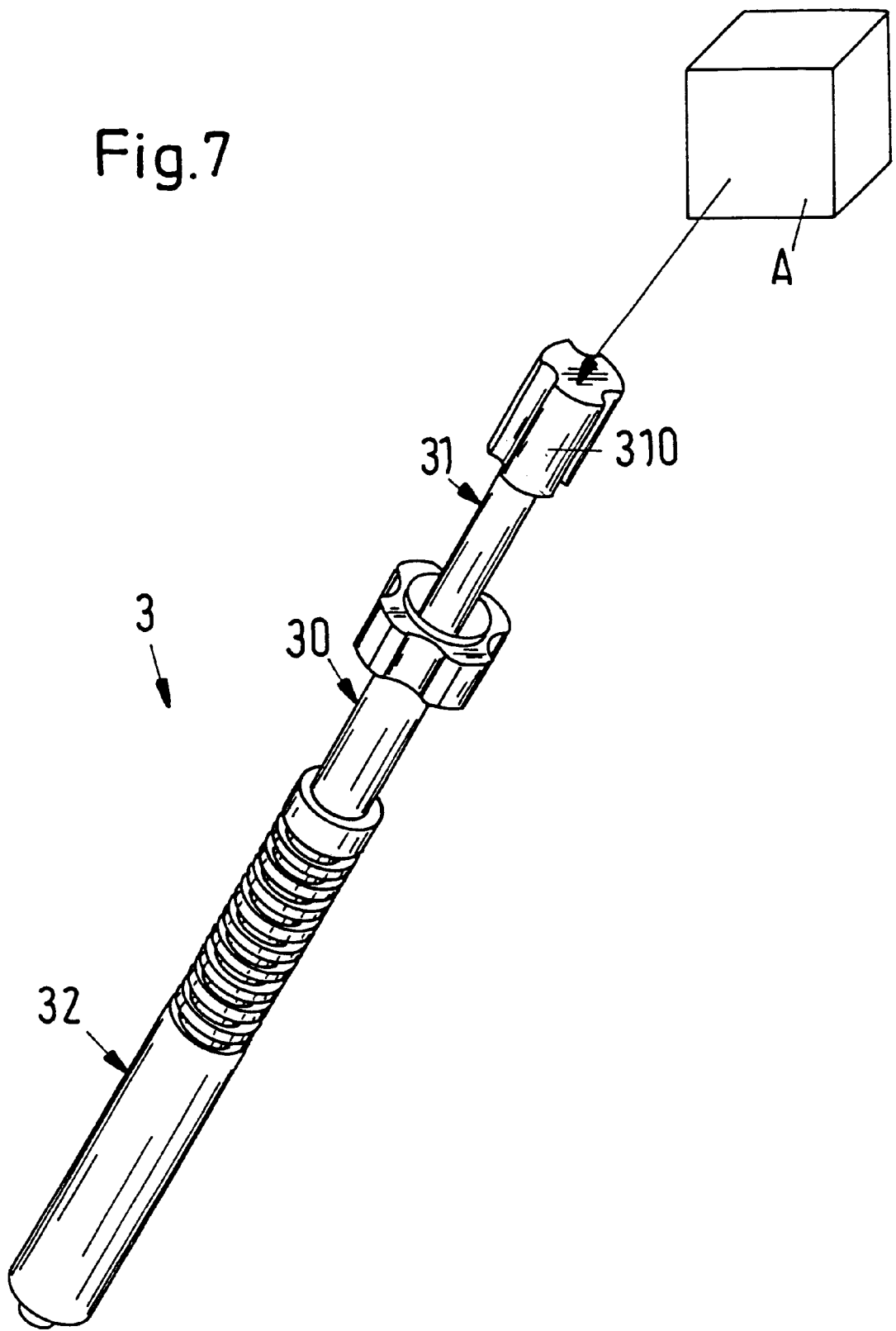

Further advantageous embodiments result from the following description of exemplary embodiments of the invention with the help of the drawing. Shown, partly schematically and/or in section, are:

FIG. 1 an exemplary embodiment of an instrument for the production of a tissue peg at a harvest location in a perspective exploded illustration, FIG. 2 the instrument of FIG. 1 in the assembled state in section, FIG. 3 the detail III (distal end) in FIG. 2 in an enlarged illustration, FIG. 4 an exemplary embodiment of an extractor for the removal of the tissue peg produced at the harvest location in the assembled state in a perspective illustration, FIG. 5 the exemplary embodiment of an extractor in accordance with FIG. 4 in section, FIG. 6 the detail VI (distal end) of the extractor of FIG. 5 in an enlarged illustration, FIG. 7 an exemplary embodiment of an instrument for the introduction of the tissue peg at the implantation location in a perspective, pulled apart illustration, FIG. 8 a cut-away of the instrument of FIG. 7 in section which illustrates the method of functioning of the instrument and FIG. 9 an exemplary embodiment of the distal end of a sleeve such as can be used in connection with an instrument in accordance with FIG. 8.

In the exemplary embodiment of an instrument 1 for the production of a tissue peg at a harvest location one recognises a reception piece 10 for the reception of a hollow borer or a hollow milling tool 11 and a sleeve 12 which is provided with a cutting edge 120 at its distal end. Once the hollow milling tool 11 is accommodated in the reception piece and firmly connected to the latter it is introduced into the sleeve 12. The reception piece 10 is provided with an abutment ring 100 which can be arrested outwardly at the reception piece at any desired location, e.g. with the help of a setting screw (not illustrated). In the introduction of the reception piece 10 with the hollow milling tool 11 into the sleeve 12 the introduction of the reception piece 10 is limited by the abutment ring 100, which strikes against the proximal end surface 121.

FIG. 2 shows the reception piece 10 which is dipped completely into the sleeve 12 up to abutment of the abutment ring 100, together with the hollow milling tool 11 which is accommodated in the reception piece 10 and fixed there—the hollow milling tool 11 can e.g. be secured with a setting screw or another suitable securing means in the reception piece 10. The distance L between the proximal end surface 121 of the sleeve 12 and the distal end of the cutting edge 120 designates the length of the sleeve 12 including the cutting edge 120. If now the hollow milling tool 11 is always secured in the reception piece 10 in the same position relative to the latter (which is as a rule predetermined through the kind of the fixing), then the position of the abutment ring 100 on the reception piece determines how deep the hollow milling tool 11 can penetrate into the tissue (e.g. the bone); the position of the abutment ring 100 thus determines the maximum length of the tissue peg to be extracted. In this it is to be observed that the length of the cutting edge 120 also plays a role herein. The sleeve 12 is namely first hammered in into the cartilage until the distal end surface 122 of the sleeve 12 lies in contact on the cartilage, thus until the cutting edge 120 has completely penetrated into the cartilage. Then the sleeve 12 can no longer slip on the elastic cartilage and the hollow milling tool 11 is ideally guided.

Markings (not illustrated) can be provided on the outer wall of the reception piece which indicate to the operating surgeon which length of the peg results from which position of the abutment ring 100, provided the hollow milling tool 11 is driven forwardly up to abutment of the abutment ring 100 against the proximal end surface 121 of the sleeve 12. This position, in which the abutment ring 100 abuts against the proximal end surface 121 of the sleeve 12, is illustrated in FIG. 2. In FIG. 3 the detail III—the distal end—is illustrated once again in enlargement.

After the termination of the milling with the hollow milling tool 11 a peg thus stands at the harvest location which is still connected at its basis (at the base of the peg) to the spongeous bone. This peg, which is covered over by a healthy cartilage layer, must now be extracted.

This takes place with the help of an extraction instrument 2 (FIG. 4) comprising a sleeve 22 which can be and as a rule also is identical to the above described sleeve 12 for the production of the peg with the help of the hollow milling tool. The sleeve 12 or 22 respectively can thus remain in place, whereas the reception piece 10 is removed together with the hollow milling tool 11 from the sleeve 12 after the production of the peg, which is still connected to the spongeous bone at its basis.

In addition to the sleeve 22 the extraction instrument 2 also comprises the actual extractor 20, which is likewise provided with an abutment ring 200 in FIG. 5 which limits the driving in of the extractor 20 into the pre-milled depression about the peg as soon namely as the abutment ring 200 abuts against the proximal end surface 221 of the sleeve 22. In the region of its distal end the extractor 20 has fins 223 which project from its inner wall. These fins 223 dig in into the peg during the driving in of the extractor 20 and enable the peg to be sheared off at its basis through a rotational movement of the extractor 20. After the shearing off of the peg the latter is located in the passage 201 of the extractor 20.

Here again it is the case that it can be indicated to the operating surgeon through markings on the outer wall of the extractor which length the peg has at which position of the abutment ring 200. In this it is again assumed that the cutting edge of the sleeve 22 has been driven into the cartilage to such an extent that the distal end surface 220 of the sleeve 22 lies in contact on the cartilage. Through this—as already mentioned—a slipping of the sleeve 22 on the cartilage is also prevented so that the extractor 20 is guided ideally in the sleeve 22. FIG. 6 shows once again the detail VI of FIG. 5 in an enlarged illustration, namely the distal end of the extraction instrument 2.

The removed peg is now located in the passage 201 of the extractor 20 and must be transported to the implantation location (not illustrated), where it is driven in into a prepared blind bore. In this the diameter of the blind bore at the implantation location (defect location) is as a rule slightly smaller than the diameter of the peg which is removed at the harvest location so that a press seating of the peg in the blind bore arises.

FIG. 7 shows an exemplary embodiment of an instrument 3 for the insertion of the peg into the blind bore produced at the implantation location. The instrument comprises a piston 31, an instrument 30 in which the peg is arranged and which can be identical to the above described extractor 20, and a sleeve 32 into which the instrument or extractor 30 respectively can be introduced. The piston 31 has at its proximal end an abutment piece 310 which can be received by a drive A and can be driven or driven forwards by the latter. The manner in which this takes place will be discussed in more detail below.

FIG. 8 shows in a section from FIG. 7 two essential details which clarify the method of functioning of the apparatus. One recognises the sleeve 32, in which the extractor 30 is pushed completely forward. The peg P is arranged in the passage 301 of the extractor 30 at the distal end of the passage 301. A buffer medium, here in the form of a Ringer solution F, such as is typically used in the operating room as a flushing solution, is arranged proximal to the peg P. Alternatively, a sodium chloride solution (cooking salt) can also be used or a soft or sponge-like plastic, the elastic module of which is less than the elastic module of the cartilage (softest part of the transplant). Where appropriate the plastic can be filled with a liquid. For the exemplary embodiment in accordance with FIG. 8, however, a liquid, namely the already named Ringer solution F, will be assumed as a buffer medium.

The piston 31 is provided with an O-ring 312 in its distal end region, thus near the front surface 311 which faces the peg P. Furthermore, one recognises that the liquid F is filled in in the passage 301 in the space between the proximal end of the peg P and the openings 302 in the wall of the extractor 30. When now the O-ring 311 slides in the distal direction past the openings 302, it seals the passage 301 and prevents the Ringer solution F from flowing backwards in the proximal direction during the pushing forward of the piston 31 in the distal direction. In this way the peg P is thus pressed out of the distal end of the sleeve 32 into the blind bore at the implantation location (not illustrated) during the pushing forward or driving forward of the piston 31 without a bodily contact existing between the piston and the peg.

In this the abutment piece 310 can form a safety abutment for the pushing forward or driving forward respectively of the piston 31. For this an abutment ring can also be provided, such as has already been discussed above. These abutments are however in principle "safety abutments"; a preferred kind of a non-mechanical "abutment" will still be discussed further below with reference to FIG. 9.

As far as the pushing forward or driving forward respectively of the piston 31 in the distal direction is concerned, it has already been mentioned further above that a continuous pushing forward of the peg P is advantageous (only a one-time overcoming of the static friction and then only sliding friction). For this purpose the drive A can continuously rotate the abutment piece 310 and thereby the piston 31. The pushing forward of the piston 31 can be caused directly in such a manner that the extractor 30 is provided with a thread 303 at its inner wall distally to the openings 302 and the piston 31 likewise has a corresponding thread on its outer wall (not illustrated) in a corresponding region. In a continuous rotation of the piston 31 the piston is then pushed forward in the distal direction in accordance with the pitch of the thread. When the distal end of the thread on the outer wall of the piston 31 then reaches the distal end of the thread 303 on the inner wall of the extractor 30, the further driving forward of the piston can also be prevented in this way. This is also a manner of realising a mechanical "safety abutment"; a preferred kind of a non-mechanical "abutment" will be explained in the following.

For this the operating surgeon must have a possibility of recognising that the peg P has been driven out of the sleeve 32 up to a desired extent. How this for example is possible is seen in FIG. 9, in which a manner is illustrated of how the distal end of the sleeve 32 can be designed. Passage openings 321 are provided in the wall of the sleeve 32 directly following the proximal end of the cutting edge 320. These passage openings 321 enable an emergence of the Ringer solution F as soon as the proximal end of the peg P frees the passage openings 321. Thereby however practically no more force is exerted on the peg P during a further pushing forward of the piston 31 since the Ringer solution F is pressed out through the passage openings 321 in a further pushing forward of the piston (non-mechanical "abutment"). Where appropriate the openings 321 could be designed in such a manner that a slight force transmission to the peg P is still possible in order still to be able to drive it over a small distance.

The method for the transplantation or the implantation respectively can thus proceed as follows: First the surgeon produces a depression (e.g. blind bore) at the implantation location (defect location) for the reception of the transplant or the implant. This can take place with the help of a conventional surgical bone drill, which can where appropriate also be guided in a sleeve. In this it is clear that the diameter of this blind bore is slightly smaller than the diameter of the peg P in order that a press seating of the peg P in the blind bore arises during the implantation of the peg.

After the production of the blind bore at the implantation location a peg P is produced which is still connected to the bone at its basis at the harvest location e.g. with the help of the instrument 1, in particular with the help of the hollow milling tool 11. Then this peg is separated from its basis and removed with the help of the instrument 2, in particular with the help of the extractor 20. In the case of an implant which is produced in vitro the peg is removed from a corresponding container. The extracted peg P is then transported to the implantation location. There the peg P can be implanted with the help of the instrument 3. This can take place in particular in such a manner that prior to the introduction of the peg P a buffer medium—such as the Ringer solution F mentioned—can first be introduced from the proximal side into the passage 301 of the extractor 30. Then the piston 31 can be introduced into the passage 301 from the proximal side. During the pushing forward or driving forward respectively of the piston 31 (e.g. by means of the drive 31 or else by hand) the enclosed Ringer solution F then drives the peg P out of the instrument 3 into the blind bore at the implantation location. It is clear that the above described instruments, in particular an entire set of instruments of this kind which are required for an operation of this kind, are particularly suitable.

What is claimed is:

1. An instrument for an introduction of an osteochondral transplant which is removed from a harvest location, or of an implant which is correspondingly prepared in vitro, at an implantation location, said instrument having a passage in which the transplant or implant respectively is received and a piston for a pressing out of the transplant or the implant respectively from a distal end of the passage into a depression which is prepared at the implantation location, wherein that a space for the reception of a buffer medium with a high conformability and an elasticity which is dimensioned in such a manner that no bodily contact between the piston and the transplant or the implant respectively exists during the pressing out of the transplant or the implant respectively is provided between an end surface of the piston facing the transplant or implant respectively and a surface of the transplant or the implant respectively facing the piston.

2. The instrument in accordance with claim 1, wherein the piston is provided with abutment means which define an end position of the piston and prevent a further pushing forward of the piston beyond the end position.

3. The instrument in accordance with claim 1, wherein the buffer medium is a fluid, and the piston is provided with a sealing means which seals off the passage and prevents a backward flowing of the fluid in a proximal direction during the pushing forward of the piston in a distal direction.

4. The instrument in accordance with claim 3, wherein the sealing means is designed as an O-ring which is arranged in a distal end region of the piston, and indeed proximally to the end surface of the piston facing the transplant.

5. The instrument in accordance with claim 4, wherein it comprises a sleeve which is provided with a cutting edge at its distal end; and in that directly following a proximal end of the cutting edge in a wall of the sleeve, passage openings are provided which enable an emergence of the fluid as soon as a proximal end of the transplant or the implant respectively frees the passage openings during the pressing out of the transplant or the implant respectively.

6. The instrument in accordance with claim 1, wherein the piston can be coupled at its proximal end to a drive which effects a continuous pushing forward of the piston.

7. The instrument in accordance with claim 1, wherein the buffer medium is designed as a soft plastic or as a sponge-like plastic, a first elastic modulus that is less than a second elastic modulus of a softest part of the transplant or the implant respectively, with it being possible for the plastic where appropriate to be filled with a liquid.

8. An instrument set for a transplantation of an osteochondral transplant or for an implantation of an implant which is correspondingly prepared in vitro, comprising an instrument for a removal of the transplant at a harvest location or, respectively, for a removal of the implant which is produced in vitro from a corresponding container, further comprising an instrument for a production of a depression at an implantation location, and comprising an instrument for an introduction of the removed transplant at the implantation location, wherein in that the instrument is designed for the introduction of the transplant or the implant respectively in accordance with claim 1.

9. The instrument set in accordance with claim 8, wherein the instrument for the removal of the transplant or the implant respectively is designed having a passage in which the transplant or implant respectively is received and a piston for a pressing out of the transplant or the implant respectively from a distal end of the passage into the depression which is prepared at the implantation location, wherein a space for the reception of a buffer medium with a high conformability and an elasticity which is dimensioned in such a manner that no bodily contact between the piston and the transplant or the implant respectively exists during the pressing out of the transplant or the implant respectively is provided between an end surface of the piston facing the transplant or implant respectively and a surface of the transplant or the implant respectively facing the piston.

10. A method for a transplantation of an osteochondral transplant or, respectively, for an implantation of a corresponding implant which is prepared in vitro, in said method a depression first being produced at an implantation location for a reception of the transplant or the implant respectively, in said method then the transplant being removed at a harvest location or the implant being removed from a corresponding container respectively, and in said method the transplant or the implant respectively finally being introduced into the depression produced at the implantation location, wherein during the transplantation or the implantation respectively an instrument in accordance with claim 1.

11. The method in accordance with claim 10, wherein during the introduction of the transplant or the implant respectively which is located in a passage of the instrument into the depression first a buffer medium and then a piston is introduced into the passage from a proximal side so that the enclosed buffer medium drives the transplant or the implant respectively out of the instrument and into the depression during a pushing forward of the piston in a distal direction.

12. The instrument in accordance which claim 3, wherein the buffer medium is a liquid.

* * * * *